(12) United States Patent
Zang

(10) Patent No.: US 12,134,645 B2
(45) Date of Patent: Nov. 5, 2024

(54) MONOCLONAL ANTIBODIES AGAINST HUMAN TIM-3

(71) Applicant: ALBERT EINSTEIN COLLEGE OF MEDICINE, Bronx, NY (US)

(72) Inventor: Xingxing Zang, New York, NY (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 926 days.

(21) Appl. No.: 17/270,405

(22) PCT Filed: Aug. 21, 2019

(86) PCT No.: PCT/US2019/047573
§ 371 (c)(1),
(2) Date: Feb. 22, 2021

(87) PCT Pub. No.: WO2020/041520
PCT Pub. Date: Feb. 27, 2020

(65) Prior Publication Data
US 2021/0198357 A1   Jul. 1, 2021

Related U.S. Application Data

(60) Provisional application No. 62/720,234, filed on Aug. 21, 2018.

(51) Int. Cl.
*C07K 16/28* (2006.01)
*A61K 39/00* (2006.01)
*A61K 47/68* (2017.01)

(52) U.S. Cl.
CPC ...... *C07K 16/2803* (2013.01); *A61K 47/6849* (2017.08); *A61K 2039/505* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| 9,321,833 | B2 | 4/2016 | Noelle |
| 9,605,070 | B2 | 3/2017 | Sabatos-Peyton et al. |
| 2006/0015952 | A1 | 1/2006 | Filvaroff |
| 2009/0197330 | A1 | 8/2009 | Numazaki et al. |

(Continued)

FOREIGN PATENT DOCUMENTS

| CN | 103079644 A | 5/2013 |
| CN | 106132991 A | 11/2016 |

(Continued)

OTHER PUBLICATIONS

Peyton et al. (2018) Blockade of Tim-3 binding to phosphatidylserine and CEACAM1 is a shared feature of anti-Tim-3 antibodies that have functional efficacy, OncoImmunology, 7:2, e1385690, Doi: 10.1080/2162402X.2017.1385690 (Year: 2018).*

(Continued)

*Primary Examiner* — Daniel E Kolker
*Assistant Examiner* — Hilary Ann Petrash
(74) *Attorney, Agent, or Firm* — Perkins Coie LLP

(57) ABSTRACT

Provided are anti-human Tim-3 IgV domain-specific antibodies and fragments thereof, as well as methods of use employing such antibodies and/or fragments.

11 Claims, 6 Drawing Sheets

Specification includes a Sequence Listing.

(56) References Cited

U.S. PATENT DOCUMENTS

| | | |
|---|---|---|
| 2012/0189617 A1 | 7/2012 | Takayanagi et al. |
| 2017/0088616 A1 | 3/2017 | Takayanagi et al. |

FOREIGN PATENT DOCUMENTS

| | | |
|---|---|---|
| JP | 2017511687 A | 4/2017 |
| WO | 2005/033144 | 4/2005 |
| WO | 2008/061013 | 5/2008 |
| WO | 2008/148884 | 12/2008 |
| WO | 2011/100538 | 8/2011 |
| WO | 2015/069794 A2 | 5/2015 |
| WO | 2015/117002 | 8/2015 |
| WO | 2015117002 A1 | 8/2015 |
| WO | 2017/153955 | 9/2017 |
| WO | 2017178493 A1 | 10/2017 |
| WO | 2018013818 A2 | 1/2018 |
| WO | 2018/036561 | 3/2018 |
| WO | 2018036561 A1 | 3/2018 |
| WO | 2018085469 A2 | 5/2018 |

OTHER PUBLICATIONS

Anderson, et al., "Tim-3:an emerging target in cancer immunotherapy landscape," Cancer Immunology Research, American Association for Cancer Research, vol. 2, No. 5, May 1, 2024, pp. 393-398.

Examination Report for European Application No. 19852182.5; Date of Mailing: Mar. 29, 2023; 8 pages.

Decision to Grant a Patent for Invention dated May 25, 2022 for allowed RU application No. 2021107091, filed Aug. 21, 2019, 17 pages with unofficial English translation.

Riechmann L .et al., "Reshaping human antibodies for therapy," Nature, 1988, v.24, n.332(6162), p. 323-327, c.326.

Vajdos, et al. "Comprehensive Functional Maps of the Antigenbinding Site of an Anti-ErbB2 Antibody Obtained with Shotgun Scanning Mutagenesis" J. Mol. Biol., 2002, v. 320, p. 415- 428, c. 416.

De Pascalis R. et al., "Grafting of "abbreviated" complementarity-determining regions containing specificity-determining residues essential for ligand contact to engineer a less immunogenic humanizedmonoclonal antibody", J Immunol., 2002, v. 169, n.6, p. 3076-3084, c. 3079.

Colman P. M., "Effects of amino acid sequence changes on antibody-antigen interactions", Research in Immunology, 1994, V. 145,N. 1, p. 33-36, c. 33.

Safdari Y. et al., "Antibody humanization methods-a review and update, Biotechnology and Genetic Engineering Reviews", 2013, V. 29, N. 2, p. 175-186, c. 178, 180.

Muller S. et al., "Spliceosomal peptide P140 for immunotherapy of systemic lupus erythematosus: results of an early phase II clinical trial," Arthritis & Rheumatism: Official Journal of the American College of Rheumatology, 2008, V. 58, N. 12, p. 3873-3883, c. 3874.

Davies J. et al., Affinity improvement of single antibody VH domains: residues in all three hypervariable regions affect antigen binding, Immunotechnology, 1996, v. 2, p. 169-179, 176- 178.

Torres M. et al., The immunoglobulin constant region contributes to affinity and specificity, Trends in immunology, 2008, V. 29, N. 2, p. 91-97, c. 93-94.

Official Action and Search Report for RU Application No. 2021107091 with unofficial translation, 34 pages.

International Search Report and Written Opinion for International Patent Appl. No. PCT/US19/47573, dated Dec. 4, 2019, 12 pages.

Extended Search Report dated Apr. 8, 2022 for co-pending EP application No. 19852182.5, filed Aug. 21, 2019, 11 pages.

Decision of Rejection in Japanese Application No. 2021-052951; Date of Mailing: Jan. 17, 2024; 8 pages.

Examination Report for European Application No. 19852182.5; Date of Mailing: Jan. 11, 2024; 4 pages.

First Office Action in Chinese Application No. 201980037800.1; Date of Mailing: Sep. 13, 2023; 8 pages.

First Office Action in Japanese Application No. 2021-502951; Date of Mailing: Jun. 27, 2023; 9 pages.

Sabatos-Peyton, et al., "Blockade of Tim-3 binding to phosphatidylserine and CEACAM1 is a shared feature of anti-Tim-3 antibodies that have functional efficacy," Oncoimmunology 2018, vol. 7, No. 2, e1385690 (9 pages).

Second Office Action in Chinese Application No. 201980037800.1; Date of Mailing: Jan. 29, 2024; 4 pages.

* cited by examiner

| Clone | Isotype | $K_{assoc}$ $(Ms)^{-1}$ | $K_{dissoc}$ $(s^{-1})$ | KD (nM) |
|---|---|---|---|---|
| 50B5 | IgG1, K | $1.87 \times 10^5$ | $2.35 \times 10^{-5}$ | 0.13 |

Fig. 3

| Clone | Isotype | $K_{assoc}$ (Ms)$^{-1}$ | $K_{dissoc}$ (s$^{-1}$) | KD (nM) |
|---|---|---|---|---|
| 15B4 | IgG1, κ | 9.1×10$^5$ | 2.9×10$^{-4}$ | 0.32 |

Fig. 6

MONOCLONAL ANTIBODIES AGAINST HUMAN TIM-3

CROSS REFERENCE TO RELATED APPLICATIONS

This present application is a 371 National Phase Application of PCT Application No. PCT/US2019/047573 entitled "MONOCLONAL ANTIBODIES AGAINST HUMAN TIM-3" filed on Aug. 21, 2019, which claims priority to U.S. Provisional Application No. 62/720,234, filed Aug. 21, 2018, the contents of each of which is hereby incorporated by reference in its entirety.

SEQUENCE LISTING

This application contains a Sequence Listing, which was submitted in ASCII format via EFS-Web, and is hereby incorporated by reference in its entirety. The ASCII copy, created on Jan. 19, 2021, is named SequenceListing.txt and is 15.7 KB in size.

BACKGROUND OF THE INVENTION

The disclosures of all publications, patents, patent application publications and books referred to herein, are hereby incorporated by reference in their entirety into the subject application to more fully describe the art to which the subject invention pertains.

T cell immunoglobulin and mucin-domain containing-3 (Tim-3), also known as Hepatitis A virus cellular receptor 2 (HAVCR2), is a type I transmembrane protein and is an inhibitory receptor that is expressed on IFN-g-producing T cells, Foxp3+ Treg cells and innate immune cells such as macrophages and dendritic cells. Tim-3 can suppress immune responses upon interaction with its ligands. Tim-3 contains a N-terminal immunoglobulin (IgV) domain, a mucin domain containing O-linked glycosylation sites, a stalk domain lying between the mucin and transmembrane domain with sites for N-linked sugars, a transmembrane domain and a cytoplasmic tail (Monney 2002). The inventor's laboratory previously reported that the IgV domain of Tim-3 is a functional domain which can bind carbohydrates (Cao 2007). Tim-3 IgV domain contains two noncanonical disulfide bonds and a unique CC'-FG cleft which is a signature structure identified in all Tim family proteins but is not in other immunoglobulin superfamily members (Cao 2007). Other also reported that adaptive resistance to therapeutic PD-1 blockade was associated with upregulation of alternative immune checkpoints including Tim-3 (Koyama 2016). In addition to carbohydrates (Cao 2007; Wilker 2007), other molecules reported to be ligands for Tim-3, including Galectin-9 (Zhu 2005), Phosphatidylserine (DeKruyff 2010), HMGB1 (high-mobility group box 1) (Chiba 2012), and LILRB2 (Leukocyte immunoglobulin like receptor B2) (POT Publ. No. WO16/111947).

SUMMARY OF THE INVENTION

An antibody or antigen-binding fragment thereof is provided which binds to an IgV domain of a human Tim-3 (T cell immunoglobulin and mucin-domain containing-3) or IgV mucin-stalk of a human Tim-3, and comprises:

a) a heavy chain comprising one or more of:

```
GYSFTGYTIN (SEQ ID NO: 1)(complementarity
determining region (CDR) 1 (CDR1));

LFNPYNGGTT (SEQ ID NO: 2) (CDR2);

ARRYYGYDAMDY (SEQ ID NO: 3) (CDR3);
or

GFNIKDYYMH (SEQ ID NO: 7) (CDR1);

WIDPENDNTIY (SEQ ID NO: 8) (CDR2);

ARDFGYVAWLVY (SEQ ID NO: 9) (CDR3); and
b) a light chain comprising one or more of:

KSSQSVLYSSNQKNHLA (SEQ ID NO: 4) (CDR1);

WASTRES (SEQ ID NO: 5) (CDR2);

HQYLSSYT (SEQ ID NO: 6) (CDR3);
or

KASQNVDTAVA (SEQ ID NO: 10) (CDR1);

SASNRYT (SEQ ID NO: 11) (CDR2);

QQYSSYPT (SEQ ID NO: 12) (CDR3).
```

An antibody or antigen-binding fragment thereof is provided which binds to an IgV domain of a human Tim-3 or IgV mucin-stalk of a human Tim-3, and comprises:
a heavy chain comprising

```
GYSFTGYTIN (SEQ ID NO: 1) (CDR1);

LFNPYNGGTT (SEQ ID NO: 2) (CDR2);

ARRYYGYDAMDY (SEQ ID NO: 3) (CDR3); and
``` a light chain comprising

```
KSSQSVLYSSNQKNHLA (SEQ ID NO: 4) (CDR1);

WASTRES (SEQ ID NO: 5) (CDR2);

HQYLSSYT (SEQ ID NO: 6) (CDR3).
```

An antibody or antigen-binding fragment thereof is provided which binds to an IgV domain of a human Tim-3 or IgV mucin-stalk of a human Tim-3, and comprises:
a heavy chain comprising

```
GFNIKDYYMH (SEQ ID NO: 7) (CDR1);

WIDPENDNTIY (SEQ ID NO: 8) (CDR2);

ARDFGYVAWLVY (SEQ ID NO: 9) (CDR3); and
``` a light chain comprising

```
KASQNVDTAVA (SEQ ID NO: 10) (CDR1);

SASNRYT (SEQ ID NO: 11) (CDR2);

QQYSSYPT (SEQ ID NO: 12) (CDR3).
```

An isolated antibody is provided which binds to an IgV domain of a human Tim-3 or IgV mucin-stalk of a human Tim-3, with an affinity of 10.0 nM $K_D$ or stronger.

A nucleic acid is provided encoding a heavy chain of an antibody which comprises one or more of:

```
GYSFTGYTIN (SEQ ID NO: 1) (CDR1);

LFNPYNGGTT (SEQ ID NO: 2) (CDR2);

ARRYYGYDAMDY (SEQ ID NO: 3) (CDR3).
```

A nucleic acid is provided encoding a heavy chain of an antibody which comprises one or more of:

```
GFNIKDYYMH (SEQ ID NO: 7) (CDR1);

WIDPENDNTIY (SEQ ID NO: 8) (CDR2);

ARDFGYVAWLVY (SEQ ID NO: 9) (CDR3).
```

A nucleic acid is provided encoding a light chain of an antibody which comprises one or more of:

```
KSSQSVLYSSNQKNHLA (SEQ ID NO: 4) (CDR1);

WASTRES (SEQ ID NO: 5) (CDR2);

HQYLSSYT (SEQ ID NO: 6) (CDR3).
```

A nucleic acid is provided encoding a light chain of an antibody which comprises one or more of:

```
KASQNVDTAVA (SEQ ID NO: 10) (CDR1);

SASNRYT (SEQ ID NO: 11) (CDR2)

QQYSSYPT (SEQ ID NO: 12) (CDR3).
```

A host cell is provided comprising one or more of the nucleic acids described herein.

An antibody or fragment thereof described herein is provided linked or conjugated to a therapeutic agent.

A method of inhibiting a human Tim-3 in a subject comprising administering an amount of an antibody or fragment thereof as described herein effective to inhibit a human Tim-3.

A method is provided of inhibiting Tim-3-mediated T cell suppression in a subject comprising administering an amount of an antibody or fragment thereof as described herein effective to inhibit Tim-3-mediated T cell suppression.

A method is provided of treating a cancer in a subject comprising administering an amount of an antibody or fragment thereof as described herein effective to treat a cancer in a subject.

A method is provided of detecting a human Tim-3-positive cell in a subject comprising administering an amount of an antibody or fragment thereof as described herein, having a detectable marker conjugated thereto, in an amount effective to label a human Tim-3-positive cell and then detecting the presence of the label in the subject, thereby detecting a human Tim-3-positive cell in a subject.

An isolated nucleic acid molecule encoding the antibody or fragment thereof as described herein is provided. In an embodiment, the nucleic acid is a DNA. In an embodiment, the nucleic acid is a cDNA. In an embodiment, the nucleic acid is an RNA.

In embodiments, the antigen-binding fragment of the antibody is a Tim-3 IgV domain-binding fragment thereof. In embodiments, the antigen-binding fragment of the antibody is a human Tim-3 IgV domain-binding fragment thereof.

A vector encoding the nucleic acid molecule described herein is provided. A host cell comprising the nucleic acid molecule described herein, or the vector described herein, is provided.

A method of producing an anti-Tim-3 IgV domain antibody, or Tim-3 IgV domain-binding fragment thereof, comprising culturing the host cell described herein, under conditions wherein the anti-Tim-3 IgV domain antibody, or Tim-3 IgV domain-binding fragment thereof, is produced by the host cell.

A pharmaceutical composition comprising an anti-Tim-3 IgV domain antibody, or Tim-3 IgV domain-binding fragment thereof, described herein, and a pharmaceutically acceptable excipient, is provided.

A method of reducing an activity of Tim-3 in a subject in need thereof is provided, comprising administering to said subject a therapeutically effective amount of the anti-Tim-3 IgV domain antibody, or Tim-3 IgV domain-binding fragment thereof, as described herein.

BRIEF DESCRIPTION OF THE DRAWINGS

FIG. 3: Kinetic parameters for 50B5 from Surface Plasmon Resonance.

FIG. 6: Kinetic parameters from Surface Plasmon Resonance.

DETAILED DESCRIPTION OF THE INVENTION

Figure 1:
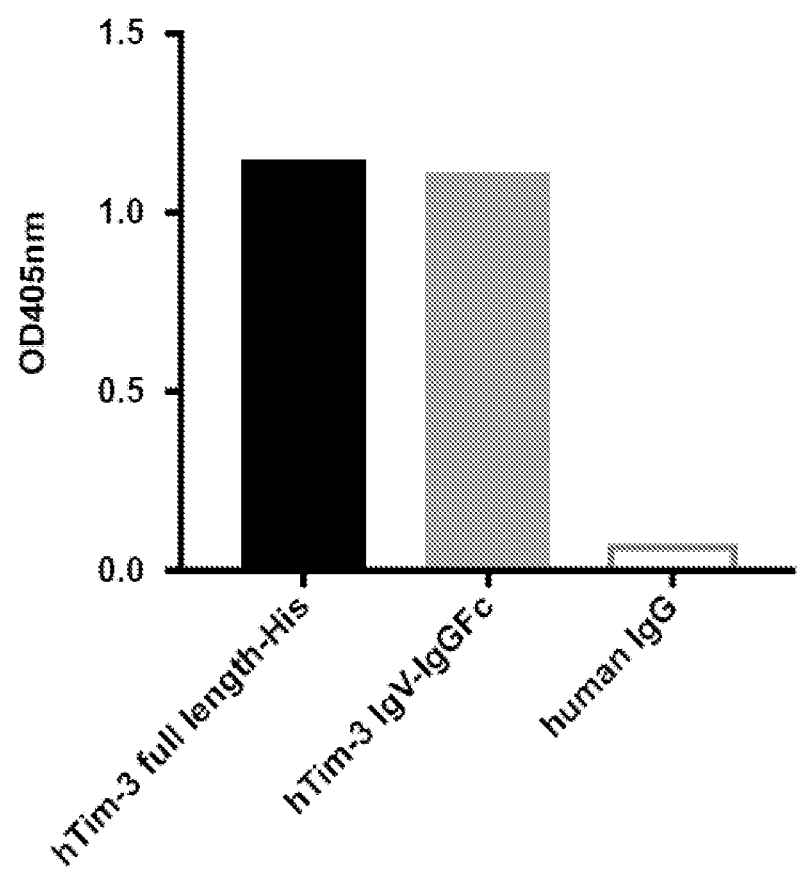
FIG. 1: ELISA shows 50B5 binds to Tim-3-IgV protein and Tim-3 whole extracellular part protein (IgVmucin-stalk), but not human IgG control protein.

An antibody or antigen-binding fragment thereof is provided which binds to an IgV domain of a human Tim-3 (T cell immunoglobulin and mucin-domain containing-3) or IgV mucin-stalk of a human Tim-3, and comprises:

a) a heavy chain comprising one or more of:

```
GYSFTGYTIN (SEQ ID NO: 1) (CDR1);

LFNPYNGGTT (SEQ ID NO: 2) (CDR2);

ARRYYGYDAMDY (SEQ ID NO: 3) (CDR3);
or

GFNIKDYYMH (SEQ ID NO: 7) (CDR1);

WIDPENDNTIY (SEQ ID NO: 8) (CDR2);

ARDFGYVAWLVY (SEQ ID NO: 9) (CDR3); and
b) a light chain comprising one or more of:

KSSQSVLYSSNQKNHLA (SEQ ID NO: 4) (CDR1);

WASTRES (SEQ ID NO: 5) (CDR2);
```

```
HQYLSSYT (SEQ ID NO: 6) (CDR3);
or

KASQNVDTAVA (SEQ ID NO: 10) (CDR1);

SASNRYT (SEQ ID NO: 11) (CDR2);

QQYSSYPT (SEQ ID NO: 12) (CDR3).
```

An antibody or antigen-binding fragment thereof is provided which binds to an IgV domain of a human Tim-3 or IgV mucin-stalk of a human Tim-3, and comprises: a heavy chain comprising

```
GYSFTGYTIN (SEQ ID NO: 1) (CDR1);

LFNPYNGGTT (SEQ ID NO: 2) (CDR2);

ARRYYGYDAMDY (SEQ ID NO: 3) (CDR3); and
a light chain comprising

KSSQSVLYSSNQKNHLA (SEQ ID NO: 4) (CDR1);

WASTRES (SEQ ID NO: 5) (CDR2);

HQYLSSYT (SEQ ID NO: 6) (CDR3).
```

An antibody or antigen-binding fragment thereof is provided which binds to an IgV domain of a human Tim-3 or IgV mucin-stalk of a human Tim-3, and comprises: a heavy chain comprising

```
GFNIKDYYMH (SEQ ID NO: 7) (CDR1);

WIDPENDNTIY (SEQ ID NO: 8) (CDR2);

ARDFGYVAWLVY (SEQ ID NO: 9) (CDR3); and
a light chain comprising

KASQNVDTAVA (SEQ ID NO: 10) (CDR1);

SASNRYT (SEQ ID NO: 11) (CDR2);

QQYSSYPT (SEQ ID NO: 12) (CDR3).
```

In embodiments, the framework regions of the light chain and the heavy chain are human framework regions, or have 85% or more identify thereto.

In embodiments, the framework regions of the light chain and the heavy chain are human framework regions. An isolated antibody or antigen-binding fragment thereof is provided which binds to an IgV domain of a human Tim-3 or IgV mucin-stalk of a human Tim-3, with an affinity of 10.0 nM $K_D$ or stronger.

In embodiments, the antibody binds to an IgV domain of a human Tim-3 or IgV mucin-stalk of a human Tim-3, with an affinity of 1.0 nM $K_D$ or stronger. In embodiments, the antibody binds to an IgV domain of a human Tim-3 or IgV mucin-stalk of a human Tim-3, with an affinity of 0.5 nM $K_D$ or stronger.

In embodiments, the antibody does not bind mouse Tim-3.

In embodiments, the antibody inhibits binding of human Tim-3 to phosphatidylserine expressed on a dexamethasone-treated Jurkat T cell.

In embodiments, the isolated antibody or antigen-binding fragment thereof has a human sequence Fc region.

In embodiments, the isolated antibody or antigen-binding fragment thereof comprises a heavy chain comprising one or more of:

```
GYSFTGYTIN (SEQ ID NO: 1) (CDR1)

LFNPYNGGTT (SEQ ID NO: 2) (CDR2)

ARRYYGYDAMDY (SEQ ID NO: 3) (CDR3).
```

In embodiments, the isolated antibody or antigen-binding fragment thereof comprises a light chain comprising one or more of:

```
KSSQSVLYSSNQKNHLA (SEQ ID NO: 4) (CDR1)

WASTRES (SEQ ID NO: 5) (CDR2)

HQYLSSYT (SEQ ID NO: 6) (CDR3).
```

In embodiments, the isolated antibody or antigen-binding fragment thereof comprises a heavy chain comprising one or more of:

```
GFNIKDYYMH (SEQ ID NO: 7) (CDR1)

WIDPENDNTIY (SEQ ID NO: 8) (CDR2)

ARDFGYVAWLVY (SEQ ID NO: 9) (CDR3).
```

In embodiments, the isolated antibody or antigen-binding fragment thereof comprises a light chain comprising one or more of

```
KASQNVDTAVA (SEQ ID NO: 10) (CDR1)

SASNRYT (SEQ ID NO: 11) (CDR2)

QQYSSYPT (SEQ ID NO: 12) (CDR3).
```

In embodiments, the isolated antibody or antigen-binding fragment thereof the antibody or fragment thereof is chimeric or humanized.

In embodiments, the isolated antibody or antigen-binding fragment thereof the antibody or fragment thereof is selected from the group consisting of a monoclonal antibody, an scFv, an Fab fragment, an Fab'fragment, and an F(ab) 'fragment. It is noted that while an scFv is not strictly a fragment of an antibody, rather it is a fusion protein, herein a fragment of an antibody includes an scFv unless otherwise excluded.

A nucleic acid is provided encoding a heavy chain of an antibody which comprises one or more of:

```
GYSFTGYTIN (SEQ ID NO: 1) (CDR1);

LFNPYNGGTT (SEQ ID NO: 2) (CDR2);

ARRYYGYDAMDY (SEQ ID NO: 3) (CDR3).
```

A nucleic acid is provided encoding a heavy chain of an antibody which comprises one or more of:

```
GFNIKDYYMH (SEQ ID NO: 7) (CDR1);

NIDPENDNTIY (SEQ ID NO: 8) (CDR2);

ARDFGYVAWLVY (SEQ ID NO: 9) (CDR3).
```

A nucleic acid is provided encoding a light chain of an antibody which comprises one or more of:

```
KSSQSVLYSSNQKNHLA (SEQ ID NO: 4) (CDR1);

WASTRES (SEQ ID NO: 5) (CDR2);

HQYLSSYT (SEQ ID NO: 6) (CDR3).
```

A nucleic acid is provided encoding a light chain of an antibody which comprises one or more of:

```
KASQNVDTAVA (SEQ ID NO: 10) (CDR1);

SASNRYT (SEQ ID NO: 11) (CDR2)

QQYSSYPT (SEQ ID NO: 12) (CDR3).
```

A host cell is provided comprising one or more of the nucleic acids described herein.

An antibody or fragment thereof described herein is provided linked or conjugated to a therapeutic agent.

In embodiments, the therapeutic agent is a cytotoxic drug, a radioactive isotope, an immunomodulator, or a second antibody.

A method of inhibiting a human Tim-3 in a subject is provided comprising administering an amount of an antibody or fragment thereof as described herein, or a human Tim3-binding fragment thereof, effective to inhibit a human Tim-3.

In embodiments, the subject has a cancer.

A method of inhibiting Tim-3-mediated T cell suppression in a subject is provided comprising administering an amount of an antibody or fragment thereof as described herein, or a human Tim3-binding fragment thereof, effective to inhibit Tim-3-mediated T cell suppression.

A method of treating a cancer in a subject is provided comprising administering an amount of an antibody or fragment thereof as described herein, effective to treat a cancer in a subject.

In embodiments, the cancer is a human Tim-3-positive cancer.

A method of detecting a human Tim-3-positive cell in a subject is provided comprising administering an amount of an antibody or fragment thereof as described herein, having a detectable marker conjugated thereto, in an amount effective to label a human Tim-3-positive cell and then detecting the presence of the label in the subject, thereby detecting a human Tim-3-positive cell in a subject.

In embodiments, the label is detected by imaging.

In embodiments, the cell is a cancer cell.

In embodiments, the cancer is a hematologic malignancy. In embodiments, the cancer is a cancer of lung, gastric, head or neck cancer, schwannoma, melanoma, or follicular B-cell non-Hodgkin lymphoma.

In embodiments, the cancer comprises a solid tumor.

In embodiments, the subject is receiving an anti-PD-1 or anti-PD-L1 or anti-CTLA4 therapy.

In embodiments, the anti-Tim-3 IgV domain antibody or Tim-3 IgV domain-binding fragment thereof, comprises (i) a VH framework comprising the framework sequence of human germline IGHV1-2*02, IGHV1-2*04, IGHV1-2*05, IGHV1-18*04, IGHV1-69-2*01, IGHV1-46*01, IGHD5-12*01, IGHD5-24*01, IGHD6-25*01, IGHJ3*01, IGHJ4*01, IGHJ4*03, IGHJ6*01, IGHJ6*02 and/or (ii) a VL framework comprising the framework sequence of human germline IGKV1-13*02, IGKV1-27*01, IGKV3-7*02, IGKV4-1*01, IGKV1D-13*02, IGKV3D-7*01, IGKJ1*01, IGKJ2*01, IGKJ4*01, IGKJ4*02.

In embodiments, the anti-Tim-3 IgV domain antibody or Tim-3 IgV domain-binding fragment thereof, binds Tim-3 IgV domain with a binding affinity ($K_D$) of from about $1 \times 10^{-9}$ M to about $1 \times 10^{-12}$ M.

In embodiments, the anti-Tim-3 IgV domain antibody or Tim-3 IgV domain-binding fragment thereof, is a monoclonal antibody.

In embodiments, the anti-Tim-3 IgV domain antibody or Tim-3 IgV domain-binding fragment thereof, is a recombinant antibody.

In embodiments, the anti-Tim-3 IgV domain antibody or Tim-3 IgV domain-binding fragment thereof, has a human framework region.

In embodiments, the anti-Tim-3 IgV domain antibody or Tim-3 IgV domain-binding fragment thereof, has a human constant region.

In embodiments, the anti-Tim-3 IgV domain antibody is provided.

In embodiments, the Tim-3 IgV domain-binding fragment of the antibody is provided.

In embodiments, the Tim-3 IgV domain-binding fragment is an Fab, F(ab)2 or scFv.

An isolated nucleic acid molecule encoding the anti-Tim-3 IgV domain antibody, or Tim-3 IgV domain-binding fragment thereof, described herein is provided. In an embodiment, the nucleic acid is a DNA. In an embodiment, the nucleic acid is a cDNA. In an embodiment, the nucleic acid is an RNA.

A vector encoding the nucleic acid molecule described herein is provided. A host cell comprising the nucleic acid molecule described herein, or the vector described herein, is provided.

A method of producing an anti-Tim-3 IgV domain antibody or Tim-3 IgV domain-binding fragment thereof, comprising culturing the host cell described herein, under conditions wherein the anti-Tim-3 IgV domain antibody or Tim-3 IgV domain-binding fragment, is produced by the host cell.

A composition is provided comprising the anti-Tim-3 IgV domain antibody or Tim-3 IgV domain-binding fragment thereof as described herein, and a carrier. In an embodiment, the composition is a pharmaceutical composition, and the carrier is a pharmaceutical carrier. A pharmaceutical composition comprising the antibody or binding fragment thereof, described herein, and a pharmaceutically acceptable excipient, is also provided.

As used herein, the term "antibody" refers to an intact antibody, i.e. with complete Fc and Fv regions. "Fragment" refers to any portion of an antibody, or portions of an antibody linked together, such as, in non-limiting examples, a Fab, F(ab)2, a single-chain Fv (scFv), which is less than the whole antibody but which is an antigen-binding portion and which competes with the intact antibody of which it is a fragment for specific binding. In this case, the antigen is the human Tim-3 IgV domain.

Such fragments can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')2, Fd, Fv, complementarity determining region (CDR) fragment, single-chain antibody (scFv), (a variable domain light chain (VL) and a variable domain heavy chain (VH) linked via a peptide linker. In an embodiment, the scFv comprises a variable domain framework sequence having a sequence identical to a human variable domain FR1, FR2, FR3 or FR4. In an embodiment, the scFv comprises a linker peptide from 5 to 30 amino acid residues long. In an embodiment, the scFv comprises a linker peptide comprising one or more of glycine, serine and threonine residues.

In an embodiment the linker of the scFv is 10-25 amino acids in length. In an embodiment the peptide linker comprises glycine, serine and/or threonine residues (see, e.g., Bird 1988 and Huston 1988, both of which are hereby incorporated by reference in their entirety), or a polypeptide that contains at least a portion of an antibody that is sufficient to confer human Tim-3 IgV domain specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk 1987, or Chothia 1989, each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an Fd fragment means an antibody fragment that consists of the VH and CH1 domains; an Fv fragment consists of the Vl and VH domains of a single arm of an antibody; and a dAb fragment (Ward 1989, hereby incorporated by reference in its entirety) consists of a VH domain. In some embodiments, fragments are at least 5, 6, 8 or 10 amino acids long. In other embodiments, the fragments are at least 14, at least 20, at least 50, or at least 70, 80, 90, 100, 150 or 200 amino acids long.

The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a human Tim-3 IgV domain antibody. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins. Thus an identified monoclonal antibody can be produced by non-hybridoma techniques, e.g. by appropriate recombinant means once the sequence thereof is identified.

In an embodiment of the inventions described herein, the antibody is isolated. As used herein, the term "isolated antibody" refers to an antibody that by virtue of its origin or source of derivation has one, two, three or four of the following: (1) is not associated with naturally associated components that accompany it in its native state, (2) is free of other proteins from the same species, (3) is expressed by a cell from a different species, and (4) does not occur in nature absent the hand of man.

In an embodiment the antibody is humanized. "Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) (or CDR) of the recipient are replaced by residues from a HVR (or CDR) of a non-human species (donor antibody) such as mouse, rat, rabbit, or nonhuman primate having the desired specificity, affinity, and/or capacity. In an embodiment, the antibody has 1, 2, 3, 4, 5, or all 6 CDR1-3 of both the heavy and light chain of the murine antibodies described herein (mAb 15B4 and mAb 50B5). In a preferred embodiment, framework (FR) residues of the murine mAb are replaced with corresponding human immunoglobulin variable domain framework (FR) residues. These may be modified further in embodiments to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all, or in embodiments substantially all, of the hypervariable loops correspond to those of a non-human immunoglobulin (e.g. mAb 15B4 and mAb 50B5 described herein), and all, or in embodiments substantially all, of the FRs are those of a human immunoglobulin sequence. The humanized antibody optionally will also comprise at least a portion of an immunoglobulin constant region (Fc), typically that of a human immunoglobulin. See, e.g., Jones 1986; Riechmann 1988; Presta 1992; Vaswani & Hamilton 1998; Harris 1995; Hurle & Gross 1994; and U.S. Pat. Nos. 6,982,321 and 7,087,409, the contents of each which are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are well known and are described in, for example, U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety. A number of "humanized" antibody molecules comprising an antigen-binding site derived from a non-human immunoglobulin have been described, including antibodies having rodent or modified rodent V regions and their associated complementarity determining regions (CDRs) fused to human constant domains. See, e.g., Winter 1991, Lobuglio 1989, Shaw 1987, and Brown 1987, the content of each of which is hereby incorporated by reference in its entirety. Other references describe rodent hypervariable regions or CDRs grafted into a human supporting framework region (FR) prior to fusion with an appropriate human antibody constant domain. See, for example, Riechmann 1988, Verhoeyen 1988, and Jones 1986, the content of each of which is hereby incorporated by reference in its entirety. Another reference describes rodent CDRs supported by recombinantly veneered rodent framework regions—European Patent Publication No. 0519596 (incorporated by reference in its entirety). These "humanized" molecules are designed to minimize unwanted immunological response toward rodent anti-human antibody molecules which limits the duration and effectiveness of therapeutic applications of those moieties in human recipients. The antibody constant region can be engineered such that it is immunologically inert (e.g., does not trigger complement lysis). See, e.g. PCT Publ. No. WO99/58572; UK Patent Application No. 9809951.8. Other methods of humanizing antibodies that may also be utilized are disclosed by Daugherty 1991; U.S. Pat. Nos. 6,180,377; 6,054,297; 5,997,867; 5,866,692; 6,210,671; and 6,350,861; and PCT Publ. No. WO01/27160, each of which is hereby incorporated by reference herein in their entirety.

Other forms of humanized antibodies have one or more, or all, CDRs (CDR L1, CDR L2, CDR L3, CDR H1, CDR H2, or CDR H3) which are altered with respect to the original antibody, which are also termed one or more CDRs "derived from" one or more CDRs from the original antibody. In an embodiment, the antibody of the invention is a humanized mAb 15B4 and mAb 50B5 with one or more, or all, CDRs (CDR L1, CDR L2, CDR L3, CDR H1, CDR H2, or CDR H3) which are altered with respect to the original antibody. In an embodiment, the antibody of the invention is a humanized mAb 15B4 and mAb 50B5 with none of its CDRs (CDR L1, CDR L2, CDR L3, CDR H1, CDR H2, or CDR H3) altered with respect to the original antibody.

In embodiments, the antibodies or fragments herein can be produced recombinantly, for example antibodies expressed using a recombinant expression vector transfected into a host cell, antibodies isolated from a recombinant, combinatorial human antibody library, antibodies isolated from an animal (e.g., a mouse) that is transgenic for human immunoglobulin genes.

In an embodiment, the anti-Tim-3 IgV domain antibody described herein is capable of specifically binding or specifically binds a human Tim-3 IgV domain. As used herein, the terms "is capable of specifically binding" or "specifically binds" refers to the property of an antibody or fragment of binding to the (specified) antigen with a dissociation constant that is <1 μM, preferably <1 nM and most preferably <10 pM. In an embodiment, the Kd of the antibody (orfragment) for Tim-3 IgV domain is better than 10.0 nM. In an embodiment, the Kd of the antibody (or fragment) for Tim-3 IgV domain is better than 1.0 nM. In an embodiment, the Kd of the antibody (or fragment) for Tim-3 IgV domain is better than 0.5 nM. In an embodiment, the Kd of the antibody (or fragment) for Tim-3 IgV domain is 0.1 nM or stronger.

The term "$K_d$", as used herein, is intended to refer to the dissociation constant of an antibody-antigen interaction. One way of determining the $K_d$ or binding affinity of antibodies to Tim-3 IgV domain is by measuring binding affinity of monofunctional Fab fragments of the antibody. (The affinity constant is the inverted dissociation constant). To obtain monofunctional Fab fragments, an antibody (for example, IgG) can be cleaved with papain or expressed recombinantly. The affinity of a fragment of an anti-human Tim-3 IgV domain antibody can be determined, for example, by surface plasmon resonance (BIAcore3000™ surface plasmon resonance (SPR) system, BIAcore Inc., Piscataway N.J.). CM5 chips can be activated with N-ethyl-N'-(3-dimethylaminopropyl)-carbodiinide hydrochloride (EDC) and N-hydroxysuccinimide (NHS) according to the supplier's instructions. The antigen can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. Serial dilutions (0.1-10× estimated $K_d$) of purified Fab samples are injected for 1 min at 100 microliters/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (see Karlsson et al. "Kinetic and concentration analysis using BIA technology, *Methods: A Companion to Methods Enzymol* 6:99-110 (1994), the content of which is hereby incorporated in its entirety) using the BIA evaluation program. Equilibrium dissociation constant ($K_d$) values are calculated as $k_{off}/k_{on}$. This protocol is suitable for use in determining binding affinity of an antibody or fragment to any antigen. Other protocols known in the art may also be used, e.g., ELISA.

An epitope that "specifically binds" to an antibody or a polypeptide is a term well understood in the art, and methods to determine such specific or preferential binding are also well known in the art. A molecular entity is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a human Tim-3 IgV domain is an antibody that binds this epitope with greater affinity, avidity, more readily, and/or with greater duration than it binds to other Tim-3 epitopes or non-Tim-3 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding.

The term "compete", as used herein with regard to an antibody, means that a first antibody, or an antigen-binding portion thereof, binds to an epitope in a manner sufficiently similar to the binding of a second antibody, or an antigen-binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the present invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

Depending on the amino acid sequences of the constant domains of their heavy chains, antibodies (immunoglobulins) can be assigned to different classes. The antibody or fragment can be, e.g., any of an IgG, IgD, IgE, IgA or IgM antibody or fragment thereof, respectively. In an embodiment the antibody is an immunoglobulin G. In an embodiment the antibody fragment is a fragment of an immunoglobulin G. In an embodiment the antibody is an IgG1, IgG2, IgG2a, IgG2b, IgG3 or IgG4. In an embodiment the antibody comprises sequences from a human IgG1, human IgG2, human IgG2a, human IgG2b, human IgG3 or human IgG4. A combination of any of these antibodies subtypes can also be used. One consideration in selecting the type of antibody to be used is the desired serum half-life of the antibody. For example, an IgG generally has a serum half-life of 23 days, IgA 6 days, IgM 5 days, IgD 3 days, and IgE 2 days. (Abbas A K, Lichtman A H, Pober J S. Cellular and Molecular Immunology, 4th edition, W.B. Saunders Co., Philadelphia, 2000, hereby incorporated by reference in its entirety).

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites. The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) (or CDRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (k) and lambda (λ), based on the amino acid sequences of their constant domains.

"Framework" or "FR" residues are those variable domain residues other than the HVR residues as herein defined.

The term "hypervariable region" or "HVR" when used herein refers to the regions of an antibody variable domain which are hypervariable in sequence and/or form structurally defined loops. Generally, antibodies comprise six HVRs; three in the VH (H1, H2, H3) and three in the VL (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. (see, e.g., Hamers-Casterman 1993; Sheriff & Constantine 1996). A number of HVR delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991) hereby incorporated by reference in its entirety). There are CDRs 1, 2, and 3 for each of the heavy and light chains. Chothia refers instead to the location of the structural loops (Chothia & Lesk 1987). The AbM HVRs represent a compromise between the Kabat HVRs and Chothia structural loops, and are used by Oxford Molecular's AbM antibody modeling software. The "contact" HVRs are based on an analysis of the available complex crystal structures. HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine of the Fc region may be removed, for example, during production or purification of the antibody, or by recombinantly engineering the nucleic acid encoding a heavy chain of the antibody. Accordingly, an intact antibody as used herein may be an antibody with or without the otherwise C-terminal lysine.

Compositions or pharmaceutical compositions comprising the antibodies, scFvs or fragments of antibodies disclosed herein are preferably comprise stabilizers to prevent loss of activity or structural integrity of the protein due to the effects of denaturation, oxidation or aggregation over a period of time during storage and transportation prior to use. The compositions or pharmaceutical compositions can comprise one or more of any combination of salts, surfactants, pH and tonicity agents such as sugars can contribute to overcoming aggregation problems. Where a composition or pharmaceutical composition of the present invention is used as an injection, it is desirable to have a pH value in an approximately neutral pH range, it is also advantageous to minimize surfactant levels to avoid bubbles in the formulation which are detrimental for injection into subjects. In an embodiment, the composition or pharmaceutical composition is in liquid form and stably supports high concentrations of bioactive antibody in solution and is suitable for inhalational or parenteral administration. In an embodiment, the composition or pharmaceutical composition is suitable for intravenous, intramuscular, intraperitoneal, intradermal and/or subcutaneous injection. In an embodiment, the composition or pharmaceutical composition is in liquid form and has minimized risk of bubble formation and anaphylactoid side effects. In an embodiment, the composition or pharmaceutical composition is isotonic. In an embodiment, the composition or pharmaceutical composition has a pH or 6.8 to 7.4.

In an embodiment the ScFvs or fragments of antibodies disclosed herein are lyophilized and/or freeze dried and are reconstituted for use.

Examples of pharmaceutically acceptable carriers include, but are not limited to, phosphate buffered saline solution, sterile water (including water for injection USP), emulsions such as oil/water emulsion, and various types of wetting agents. Preferred diluents for aerosol or parenteral administration are phosphate buffered saline or normal (0.9%) saline, for example 0.9% sodium chloride solution, USP. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, the content of each of which is hereby incorporated in its entirety). In non-limiting examples, the can comprise one or more of dibasic sodium phosphate, potassium chloride, monobasic potassium phosphate, polysorbate 80 (e.g., 2-[2-[3,5-bis(2-hydroxyethoxy)oxolan-2-yl]-2-(2-hydroxyethoxy)ethoxy]ethyl(E)-octadec-9-enoate), disodium edetate dehydrate, sucrose, monobasic sodium phosphate monohydrate, and dibasic sodium phosphate dihydrate.

The antibodies, or fragments of antibodies, or compositions, or pharmaceutical compositions described herein can also be lyophilized or provided in any suitable forms including, but not limited to, injectable solutions or inhalable solutions, gel forms and tablet forms.

The term "Fc domain" herein is used to define a C-terminal region of an immunoglobulin heavy chain, including native sequence Fc regions and variant Fc regions. Although the boundaries of the Fc domain of an immunoglobulin heavy chain might vary, the human IgG heavy chain Fc domain is usually defined to stretch from an amino acid residue at position Cys226, or from Pro230, to the carboxyl-terminus thereof. The C-terminal lysine of the Fc domain may be removed, for example, by recombinantly engineering the nucleic acid encoding it. In embodiments, the antibody comprises an Fc domain. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2-CH3 domain interface to increase the affinity of IgG for FcRn at acidic but not neutral pH (Dall'Acqua 2006; Yeung 2009). In an embodiment, the Fc domain has the same sequence as a human IgG1 Fc domain.

In embodiments, the invention encompasses modifications to the variable regions disclosed herein. For example, the invention includes antibodies comprising functionally equivalent variable regions and CDRs which do not significantly affect their properties as well as variants which have enhanced or decreased activity and/or affinity. For example, the amino acid sequence may be mutated to obtain an antibody with the desired binding affinity to human Tim-3 IgV. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but framework alterations are also contemplated. Conservative substitutions are shown in Table 1 under the heading of "conservative substitutions." If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a R-sheet or helical conformation, (b) the charge or hydrophobicity of the molecule at the target site, or (c) the bulk of the side chain. Naturally occurring residues are divided into groups based on common side-chain properties:
 (1) Non-polar: Norleucine, Met, Ala, Val, Leu, lie;
 (2) Polar without charge: Cys, Ser, Thr, Asn, Gln;
 (3) Acidic (negatively charged): Asp, Glu;
 (4) Basic (positively charged): Lys, Arg;
 (5) Residues that influence chain orientation: Gly, Pro; and
 (6) Aromatic: Trp, Tyr, Phe, His.

Non-conservative substitutions are made by exchanging a member of one of these classes for another class.

One type of substitution, for example, that may be made is to change one or more cysteines in the antibody, which may be chemically reactive, to another residue, such as, without limitation, alanine or serine. For example, there can be a substitution of a non-canonical cysteine. The substitution can be made in a CDR or framework region of a variable domain or in the constant region of an antibody. In some embodiments, the cysteine is canonical. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

The antibodies may also be modified, e.g. in the variable domains of the heavy and/or light chains, e.g., to alter a binding property of the antibody. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. For example, a mutation may be made in one or more of the CDR regions to increase or decrease the $K_D$ of the antibody for human Tim-3 IgV domain, to increase or decrease $k_{off}$, or to alter the binding specificity of the antibody. Techniques in site-directed mutagenesis are well-known in the art.

A modification or mutation may also be made in a framework region or constant region to increase the half-life of an anti-human Tim-3 IgV domain antibody. See, e.g., PCT Publication No. WO 00/09560. A mutation in a framework region or constant region can also be made to alter the immunogenicity of the antibody, to provide a site for covalent or non-covalent binding to another molecule, or to alter such properties as complement fixation, FcR binding and antibody-dependent cell-mediated cytotoxicity. According to the invention, a single antibody may have mutations in any one or more of the CDRs or framework regions of the variable domain or in the constant region.

In an embodiment, an antibody described herein is recombinantly produced. In an embodiment, the fusion protein is produced in a eukaryotic expression system.

In an embodiment, the fusion protein produced in the eukaryotic expression system comprises glycosylation at a residue on the Fc portion corresponding to Asn297.

In an embodiment the composition or pharmaceutical composition comprising the antibody, or antigen-binding fragment thereof, described herein is substantially pure with regard to the antibody, or antigen-binding fragment thereof. A composition or pharmaceutical composition comprising the antibody, or antigen-binding fragment thereof, described herein is "substantially pure" with regard to the antibody or fragment when at least 60% to 75% of a sample of the composition or pharmaceutical composition exhibits a single species of the antibody, or antigen-binding fragment thereof. A substantially pure composition or pharmaceutical composition comprising the antibody, or antigen-binding fragment thereof, described herein can comprise, in the portion thereof which is the antibody, or antigen-binding fragment, 60%, 70%, 80% or 90% of the antibody, or antigen-binding fragment, of the single species, more usually about 95%, and preferably over 99%. Purity or homogeneity may be tested by a number of means well known in the art, such as polyacrylamide gel electrophoresis or HPLC.

In an embodiment, the human Tim3 has the following sequence:

(SEQ ID NO: 13)
MFSHLPFDCVLLLLLLLLTRSSEVEYRAEVGQNAYLPCFYTPAAPGNLV

PVCWGKGACPVFECGNVVLRTDERDVNYWTSRYWLNGDFRKGDVSLTIE

-continued
NVTLADSGIYCCRIQIPGIMNDEKFNLKLVIKPAKVTPAPTRQRDFTAA

FPRMLTTRGHGPAETQTLGSLPDINLTQISTLANELRDSRLANDLRDSG

ATIRIGIYIGAGICAGLALALIFGALIFKWYSHSKEKIQNLSLISLANL

PPSGLANAVAEGIRSEENIYTIEENVYEVEEPNEYYCYVSSRQQPSQPL

GCRFAMP

In an embodiment, an IgV domain sequence of the antibody comprises:

(SEQ ID NO: 22)
SEVEYRAEVGQNAYLPCFYTPAAPGNLVPVCWGKGACPVFECGNVVLRT

DERDVNYWTSRYWLNGDFRKGDVSLTIENVTLADSGIYCCRIQIPGIMN

DEKFNLKLVIKPA

"And/or" as used herein, for example, with option A and/or option B, encompasses the separate embodiments of (i) option A, (ii) option B, and (iii) option A plus option B.

All combinations of the various elements described herein are within the scope of the invention unless otherwise indicated herein or otherwise clearly contradicted by context.

This invention may be better understood from the Experimental Details, which follow.

EXAMPLES

Generation of mAbs specifically bind to the IgV domain of human Tim-3: A Tim-3 IgV-Ig fusion protein was generated by fusing the human Tim-3 IgV coding region (S22-A132) to a human IgG1 Fc tag of plasmid pMT/BiP as previously described (Zhao 2013). The fusion protein was expressed in a S2 system and then purified. Mice were immunized with Tim-3 IgV-Ig fusion protein and hybridomas were generated by standard techniques from splenocytes fused to NSO myeloma cells.

Figure 2:
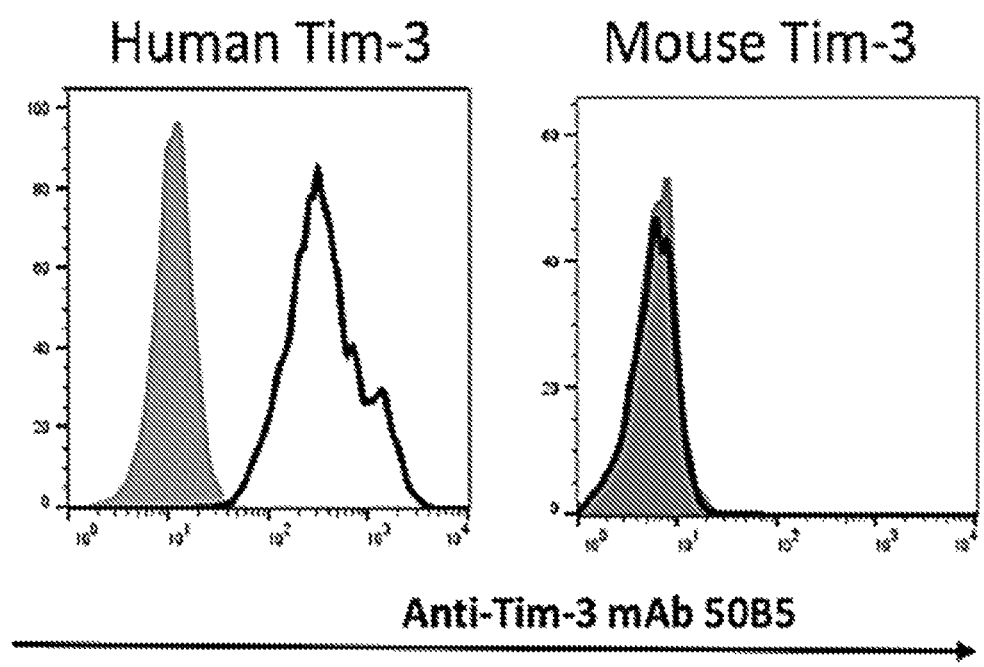
FIG. 2. FACS shows 50B5 bind to cell lines expressing human Tim-3, but not mouse Tim-3. 50B5 (open histograms) or mouse IgG1 isotype control (shaded histograms)

Characterization of mAb 50B5: mAb 50B5 was generated. It is IgG1 with kappa chain. It bound both Tim-3-IgV protein and Tim-3 whole extracellular part protein (IgV-mucin-stalk), but not human IgG protein, in ELISA assay (FIG. 1). It was confirmed that 50B5 bound to human Tim-3, but not mouse Tim-3, expressed on cell lines in FACS (FIG. 2).

Figures 4A, 4B:
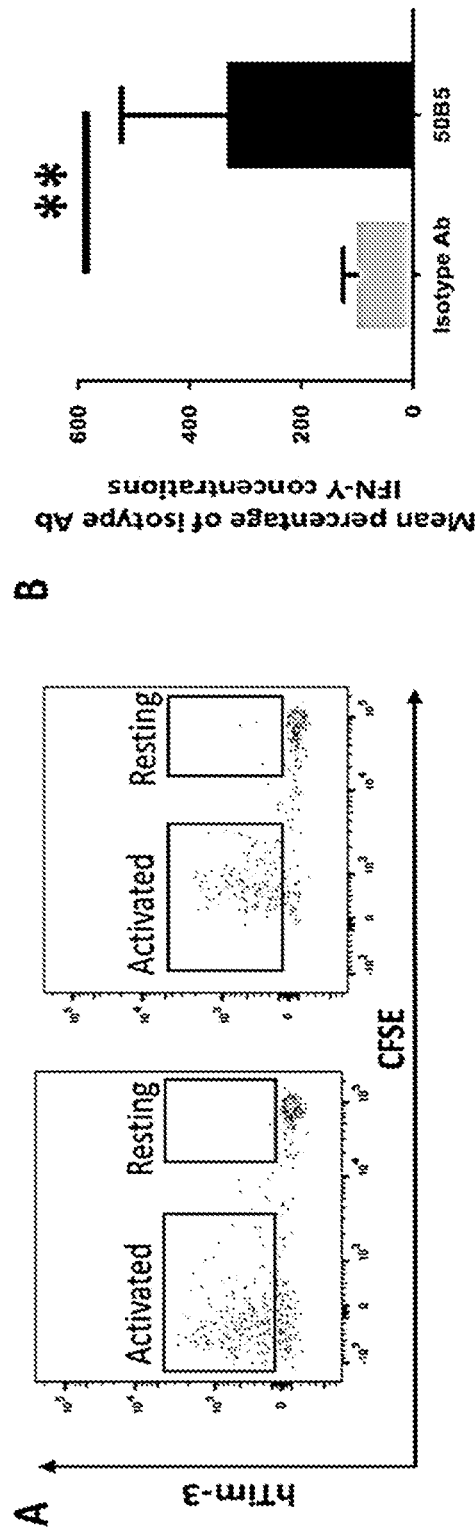
FIG. 4A-4B: 4A: In mixed lymphocyte reaction assay, divided CD4 and CD8 T cells, but not undivided CD4 and CD8T cells, expressed Tim-3 on day 4. 4B: mAb 50B5 significantly enhanced IFN-g production from CD4 and CD8 T cells on day 4 in mixed lymphocyte reaction assay; N=8; ** P<0.01

By Surface Plasmon Resonance method, the binding affinity of mAb 50B5 to human Tim-3 protein was determined to be 0.13 nM $K_D$ (FIG. 3). To determine the blocking function of mAb 50B5, a binding assay was performed and it was found that mAb 50B5 blocked the binding of human Tim-3 to phosphatidylserine expressed on dexamethasone-treat Jurkat T cells. As Tim-3 is an inhibitory receptor that is expressed on IFN-g-producing T cells, mixed lymphocyte reaction was used to test the antagonist ability of mAb 50B5. Mature Dendritic cells, which were differentiated from monocytes from PBMC from one donor, were incubated with purified T cells, which were from PBMC from another donor, for four days. Divided CD4 T cells and divided CD8 T cells were found, but not the undivided CD4 and CD8 T cells, expressed Tim-3 on their surface (FIG. 4A). In the mixed lymphocyte reaction, mAb 50B5 or the control mouse IgG1 was added, and it was found mAb 50B5 increased IFN-g production more than three times than control IgG1 (FIG. 4B).

Taken together, these results demonstrate that mAb 50B5 is an antagonist antibody against human Tim-3. Finally, mAb 50B5 hybridoma was sequenced and it was found that the mAb had the unique sequences of VH and VL.

50B5 Heavy Chain: DNA Sequence (414 bp)
  Leader sequence-FR1-CDR1-FR2-CDR2-FR3-CDR3-FR4
  (Leader sequence bolded, CDRs1-3 underlined):

(SEQ ID NO: 14)
ATGGGATGGAGCTGGATCTTTCTCTTCCTCCTGTCAGGAACTGCAGGTG

TCCACTCTGAGGTCCAGCTGCAACAGTCTGGACCTGAGCTGGTGAAGCC

TGGAGCTTCAATGAAGATATCCTGCAAGGCTTCT<u>GGTTACTCATTCACT</u>

<u>GGCTACACCATAAAC</u>TGGGTGAAGCAGAGCCATGGAAAGAACCTTGAGT

GGATTGGAC<u>TTTTTAATCCTTACAATGGTGGTACTACCTTCAACCAGAA</u>

<u>G</u>TTCAAGGGCAAGGCCACATTAACTGTTGACAAGTCATCCAGCACAGCC

TACATGGAGCTCCTCAGTCTGACATCTGAGGACTCTGCAGTCTATTACT

GT<u>GCAAGACGATACTACGGCTACGATGCTATGGACTAC</u>TGGGGTCAAGG

AACCTCAGTCACCGTCTCCTCA

50B5 Heavy Chain: Amino Acids Sequence (138 aa)
  Leader sequence-FR1-CDR1-FR2-CDR2-FR3-CDR3-FR4
  (Leader sequence bolded, CDRs1-3 underlined):

(SEQ ID NO: 15)
MGWSWIFLFLLSGTAGVHSEVQLQQSGPELVKPGASMKISCKASG<u>YSFT</u>

<u>GYTINW</u>VKQSHGKNLEWIG<u>LFNPYNGGTTFNQKFKG</u>KATLTVDKSSSTA

YMELLSLTSEDSAVYYC<u>ARRYYGYDAMDY</u>WGQGTSVTVSS

50B5 Light Chain: DNA Sequence (396 bp)
  Leader sequence-FR1-CDR1-FR2-CDR2-FR3-CDR3-FR4
  (Leader sequence bolded, CDRs1-3 underlined):

(SEQ ID NO: 16)
ATGGAATCACAGACTCAGGTCTTCCTCTCCCTGCTGCTCTGGGTATCTG

GTACCTGTGGGAACATTATGATGACACAGTCGCCATCATCTCTGCTGT

GTCTGCAGGAGAAAAGGTCACTATGAGCTGT<u>AAGTCCAGTCAAAGTGTT</u>

<u>TTATACAGTTCAAATCAGAAGAACCACTTGGCC</u>TGGTACCAGCAGAAAC

CAGGGCAGTCTCCTAAACTGCTAATCTAC<u>TGGGCATCCACTAGGGAATC</u>

TGGTGTCCCTGATCGCTTCACAGGCAGTGGATCTGGGACAGATTTTACT

CTTACCATCAGCAGTGTACAAGCTGAAGACCTGGCAGTTTATTACTGTC

<u>ATCAATACCTCTCCTCGTACACG</u>TTCGGAGGGGGGACCAAGCTGGAAAT

TAAG

50B5 Light Chain: Amino Acids Sequence (132 aa)
  Leader sequence-FR1-CDR1-FR2-CDR2-FR3-CDR3-FR4
  (Leader sequence bolded, CDRs1-3 underlined):

(SEQ ID NO: 17)
MESQTQVFLSLLLWVSGTCGNIMMTQSPSSLAVSAGEKVTMSC<u>KSSQSV</u>

<u>LYSSNQKNHLA</u>WYQQKPGQSPKLLIY<u>WASTRESG</u>VPDRFTGSGSGTDFT

LTISSVQAEDLAVYYC<u>HQYLSSYT</u>FGGGTKLEIK

Figure 5:
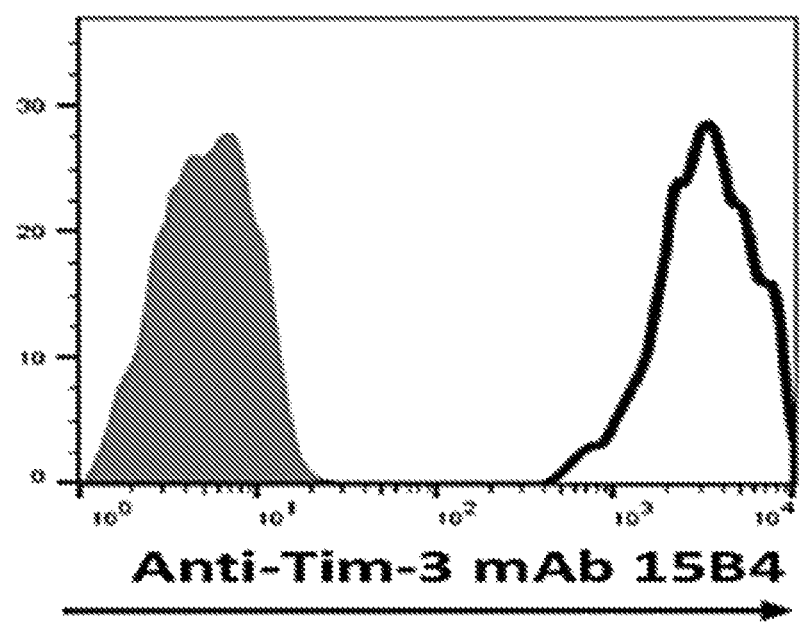
FIG. 5: FACS shows 15B4 bind to a cell line expressing human Tim-3. 15B4 (open histograms) or mouse IgG1 isotype control (shaded histograms).

Characterization of mAb 15B4: Another mAb, 15B4, was generated by the same technique as above. mAb 15B4 is IgG1 with kappa chain, and binds to human Tim-3 expressed on cell lines in FACS (FIG. 5). By Surface Plasmon Resonance method, it was determined that the binding affinity of mAb 15B4 to human Tim-3 protein was 0.32 nM KD (FIG. 6). To determine the blocking function of mAb 15B4, a binding assay was performed and it was found that 15B4 blocked the binding of human Tim-3 to phosphatidylserine expressed on dexamethasone-treat Jurkat T cells. Finally, the 15B4 hybridoma was sequenced and it was found the mAb had the unique sequences of VH and VL:

15B4 Heavy Chain: DNA Sequence (414 bp):
  Leader sequence-FR1-CDR1-FR2-CDR2-FR3-CDR3-FR4
  (Leader sequence bolded, CDRs1-3 underlined):

(SEQ ID NO: 18)
ATGGAATGGAGCTGGGTCTTTCTCTTCCTGATGGCAGTGGTTACAGGGG

TCAATTCAGAGGTTCAGCTGCAGCAGTCTGGGGCTGAGGTTGTGAGGCC

AGGGGCCTTAGTCAAGTTGTCCTGCAAAGCTTCT<u>GGCTTCAACATTAAA</u>

<u>GACTACTATATGCAC</u>TGGGTGAGGCAGAGGCCTGAACAGGGCCTGGAGT

GGATTGGAT<u>GGATTGATCCTGAGAATGACAATACTATATATGACCCGAA</u>

<u>G</u>TTCCAGGACAGGGCCAGTATAACAGCAGACACATCCTCCAACACAGCC

TACCTGCAGCTCAGCAGCCTGACATCTGAGGACACTGCCGTCTATTACT

GT<u>GCTAGGGACTTCGGCTACGTAGCCTGGCTTGTTTAC</u>TGGGGCCAAGG

GACTCTGGTCACTGTCTCTGCA.

15B4 Heavy Chain: Amino Acids Sequence (138 aa):
  Leader sequence-FR1-CDR1-FR2-CDR2-FR3-CDR3-FR4
  (Leader sequence bolded, CDRs1-3 underlined):

(SEQ ID NO: 19)
MEWSWVFLFLMAVVTGVNSEVQLQQSGAEVVRPGALVKLSCKASG<u>FNIK</u>

<u>DYYMH</u>WVRQRPEQGLEWIG<u>WIDPENDNTIYDPKFQD</u>RASITADTSSNTA

YLQLSSLTSEDTAVYYC<u>ARDFGYVAWLVY</u>WGQGTLVTVSA.

15B4 Light Chain: DNA Sequence (378 bp):
  Leader sequence-FR1-CDR1-FR2-CDR2-FR3-CDR3-FR4
  (Leader sequence bolded, CDRs1-3 underlined):

(SEQ ID NO: 20)
ATGTCACAGTCTCAGGTCTTTGTATTCGCGTTTCTCTGGTTGTCTGGTG

TTGATGGAGACATTGTGATGACCCAGTCTCAAGAATTCATGTCCACATC

```
AGTAGGAGACAGGGTCAGCATCACCTGCAAGGCCAGTCAGAATGTGGAT

ACTGCTGTAGCCTGGTATCAACAGAAACCAGGACAATCTCCTAAACTAC

TGATTTACTCGGCATCCAATCGGTACACTGGAGTCCCTGATCGCTTCAC

AGGCACTGGATCTGGGACAGATTTCACTCTCACCATCAACAATATGCAG

TCTGAAGACCTGGCAGATTATTTCTGCCAGCAATATAGCAGCTATCCA

CGTTCGGAGGGAGGACCAAGCTGGAAATAAAACGG.
```

15B4 Light Chain: Amino Acids Sequence (126 aa):
  Leader sequence-FR1-CDR1-FR2-CDR2-FR3-CDR3-FR4
  (Leader sequence bolded, CDRs1-3 underlined):

```
                                         (SEQ ID NO: 21)
MSQSQVFVFAFLWLSGVDGDIVMTQSQEFMSTSVGDRVSITCKASQNVD

TAVAWYQQKPGQSPKLLIYSASNRYTGVPDRFTGTGSGTDFTLTINNMQ

SEDLADYFCQQYSSYPTFGGRTKLEIKR.
```

REFERENCES

Bird et al. Science 242(4877):423-426 (1988)
Brown et al. Cancer Res 47(13):3577-3583 (1987)
Cao et al. Immunity 26(3):311-321 (2007)
Chiba et al. Nat Immunol 13(9):832-842 (2012)
Chothia & Lesk J Mol Biol 196(4):901-917 (1987)
Chothia et al. Nature 342(6252):877-883 (1989)
Dall'Acqua et al. J Biol Chem 281(33):23514-23524 (2006)
Daugherty et al. Nucleic Acids Res 19(9):2471-2476 (1991)
DeKruyff et al. J Immunol 184(4):1918-1930 (2010)
Hamers-Casterman et al. Nature 363(6428):446-448 (1993)
Harris Biochem Soc Trans 23(4):1035-1038 (1995)
Hurle & Gross Curr Opin Biotechnol 5(4):428-433 (1994)
Huston et al. Proc Natl Acad Sci USA 85(16):5879-5883 (1988)
Jones et al. Nature 321(6069):522-525 (1986)
Koyama et al. Nat Commun 7:10501 (2016)
Lobuglio et al. Proc Natl Acad Sci USA 86(11):4220-4224 (1989)
Monney et al. Nature 415(6871):536-541 (2002)
Presta Curr Opin Biotechnol 3(4):394-398 (1992)
Riechmann et al. Nature 332(6162):323-327 (1988)
Shaw et al. J Immunol 138(12):4534-4538 (1987)
Sheriff & Constantine Nat Struct Biol 3(9):733-736 (1996)
Vaswani & Hamilton Ann Allergy Asthma Immunol 81(2):105-115 (1998)
Verhoeyen et al. Science 239(4847):1534-1536 (1988)
Ward et al. Nature 341(6242):544-546 (1989)
Wilker et al. Int Immunol 19(6):763-773 (2007)
Winter et al. Nature 349(6307):293-299 (1991)
Yeung et al. J Immunol 182:7663-7671 (2009)
Zhao et al. Proc Natl Acad Sci USA 110(24):9879-9884 (2013)
Zhu et al. Nat Immunol 6(12):1245-1252 (2005)

What is claimed is:

1. An antibody or antigen-binding fragment thereof which binds to an IgV domain of a human Tim-3 (T cell immunoglobulin and mucin-domain containing-3) or IgV mucin-stalk of a human Tim-3, and comprises:

a)

```
GYSFTGYTIN (SEQ ID NO: 1) (HCDR1);
LFNPYNGGTT (SEQ ID NO: 2 (HCDR2);
ARRYYGYDAMDY (SEQ ID NO: 3) (HCDR3);
KSSQSVLYSSNQKNHLA (SEQ ID NO: 4) (LCDR1);
WASTRES (SEQ ID NO: 5) (LCDR2); and
HQYLSSYT (SEQ ID NO: 6) (LCDR3); or GFNIKDYYMH (SEQ ID NO: 7) (HCDR1);
WIDPENDNTIY (SEQ ID NO: 8) (HCDR2);
ARDFGYVAWLVY (SEQ ID NO: 9) (HCDR3);
KASQNVDTAVA (SEQ ID NO: 10) (LCDR1);
SASNRYT (SEQ ID NO: 11) (LCDR2); and
QQYSSYPT (SEQ ID NO: 12) (LCDR3).
```

2. The antibody or antigen-binding fragment thereof of claim 1 comprising:

```
GYSFTGYTIN (SEQ ID NO: 1) (HCDR1);
LFNPYNGGTT (SEQ ID NO: 2) (HCDR2);
ARRYYGYDAMDY (SEQ ID NO: 3) (HCDR3);
KSSQSVLYSSNQKNHLA (SEQ ID NO: 4) (LCDR1);
WASTRES (SEQ ID NO: 5) (LCDR2); and
HQYLSSYT (SEQ ID NO: 6) (LCDR3).
```

3. The antibody or antigen-binding fragment thereof of claim 1 comprising:

```
GFNIKDYYMH (SEQ ID NO: 7) (HCDR1);
WIDPENDNTIY (SEQ ID NO: 8) (HCDR2);
ARDFGYVAWLVY (SEQ ID NO: 9) (HCDR3);
KASQNVDTAVA (SEQ ID NO: 10) (LCDR1);
SASNRYT (SEQ ID NO: 11) (LCDR2); and
QQYSSYPT (SEQ ID NO: 12) (LCDR3).
```

4. The antibody or antigen-binding fragment thereof of claim 1, wherein the framework regions of the light and heavy chains have at least 85% identity to human framework regions.

5. The antibody or antigen-binding fragment thereof of claim 1, which binds to an IgV domain of a human Tim-3 or IgV mucin-stalk of a human Tim-3, with an affinity of 10.0 nM $K_D$ or less.

6. The antibody or antigen-binding fragment thereof of claim 5, which binds to an IgV domain of a human Tim-3 or IgV mucin-stalk of a human Tim-3, with an affinity of 0.5 nM $K_D$ or less.

7. The antibody or antigen-binding fragment thereof of claim 1, which has a human Fc region.

8. The antibody or antigen-binding fragment thereof of claim 5, which inhibits binding of human Tim-3 to phosphatidylserine expressed on a dexamethasone-treated Jurkat T cell.

9. The antibody or antigen-binding fragment thereof of claim 1, wherein the antibody or antigen-binding fragment thereof is chimeric or humanized.

10. The antibody or antigen-binding fragment thereof of claim 1, wherein the antibody or antigen-binding fragment thereof is selected from the group consisting of a monoclonal antibody, an scFv, a Fab fragment, a Fab'fragment, and an F(ab)'fragment.

11. The antibody or antigen-binding fragment thereof of claim 1, which is linked or conjugated to a therapeutic agent selected from the group consisting of a cytotoxic drug, a radioactive isotope, an immunomodulator, and a second antibody.

* * * * *

UNITED STATES PATENT AND TRADEMARK OFFICE
CERTIFICATE OF CORRECTION

PATENT NO. : 12,134,645 B2  
APPLICATION NO. : 17/270405  
DATED : November 5, 2024  
INVENTOR(S) : Xingxing Zang Page 1 of 1

It is certified that error appears in the above-identified patent and that said Letters Patent is hereby corrected as shown below:

In the Specification

In Column 6, Line 62, delete "NIDPENDNTIY" insert -- WIDPENDNTIY -- therefore.

Signed and Sealed this  
Eleventh Day of March, 2025

Coke Morgan Stewart  
*Acting Director of the United States Patent and Trademark Office*

SEQUENCE LISTING

```
<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: 50B5 HCDR1

<400> SEQUENCE: 1

Gly Tyr Ser Phe Thr Gly Tyr Thr Ile Asn
1               5                   10

<210> SEQ ID NO 2
<211> LENGTH: 10
<212> TYPE: PRT
<213> ORGANISM: Artificial Sequence
<220> FEATURE:
<223> OTHER INFORMATION: 50B5 HCDR2

<400> SEQUENCE: 2

Leu Phe Asn Pro Tyr Asn Gly Gly Thr Thr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: 50B5 HCDR3

<400> SEQUENCE: 3

Ala Arg Arg Tyr Tyr Gly Tyr Asp Ala Met Asp Tyr
1               5                   10
```

```
<210> SEQ ID NO 4
<211> LENGTH: 17
<212> TYPE: PRT
<213> ORGANISM: Artificial Sequence
<220> FEATURE:
<223> OTHER INFORMATION: 50B5 LCDR1

<400> SEQUENCE: 4

Lys Ser Ser Gln Ser Val Leu Tyr Ser Ser Asn Gln Lys Asn His Leu
1               5                   10                  15
Ala

<210> SEQ ID NO 5
<211> LENGTH: 7
<212> TYPE: PRT
<213> ORGANISM: Artificial Sequence
<220> FEATURE:
<223> OTHER INFORMATION: 50B5 LCDR2

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: 50B5 LCDR3

<400> SEQUENCE: 6

His Gln Tyr Leu Ser Ser Tyr Thr
1               5

<210> SEQ ID NO 7
<211> LENGTH: 10
<212> TYPE: PRT
<213> ORGANISM: Artificial Sequence
<220> FEATURE:
<223> OTHER INFORMATION: 15B4 HCDR1

<400> SEQUENCE: 7

Gly Phe Asn Ile Lys Asp Tyr Tyr Met His
1               5                   10

<210> SEQ ID NO 8
<211> LENGTH: 11
<212> TYPE: PRT
<213> ORGANISM: Artificial Sequence
<220> FEATURE:
<223> OTHER INFORMATION: 15B4 HCDR2

<400> SEQUENCE: 8

Trp Ile Asp Pro Glu Asn Asp Asn Thr Ile Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: 15B4 HCDR3

<400> SEQUENCE: 9

Ala Arg Asp Phe Gly Tyr Val Ala Trp Leu Val Tyr
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: 15B4 LCDR1

<400> SEQUENCE: 10

Lys Ala Ser Gln Asn Val Asp Thr Ala Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: 15B4 LCDR2

<400> SEQUENCE: 11

Ser Ala Ser Asn Arg Tyr Thr
1               5

<210> SEQ ID NO 12
<211> LENGTH: 8
<212> TYPE: PRT
<213> ORGANISM: Artificial Sequence
<220> FEATURE:
<223> OTHER INFORMATION: LCDR3

<400> SEQUENCE: 12

Gln Gln Tyr Ser Ser Tyr Pro Thr
1               5

<210> SEQ ID NO 13
<211> LENGTH: 301
<212> TYPE: PRT
<213> ORGANISM: Homo sapiens

<400> SEQUENCE: 13

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
                20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
        50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

```
Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
            245                 250                 255

Gly Ile Arg Ser Glu Glu Asn Ile Tyr Thr Ile Glu Glu Asn Val Tyr
        260                 265                 270

Glu Val Glu Glu Pro Asn Glu Tyr Tyr Cys Tyr Val Ser Ser Arg Gln
            275                 280                 285

Gln Pro Ser Gln Pro Leu Gly Cys Arg Phe Ala Met Pro
        290                 295                 300
```

```
<210> SEQ ID NO 14
<211> LENGTH: 414
<212> TYPE: DNA
<213> ORGANISM: Artificial Sequence
<220> FEATURE:
<223> OTHER INFORMATION: 50B5 heavy chain
<220> FEATURE:
<221> NAME/KEY: misc_feature
<222> LOCATION: (1)..(57)
<223> OTHER INFORMATION: Leader sequence
<220> FEATURE:
<221> NAME/KEY: misc_feature
<222> LOCATION: (133)..(162)
<223> OTHER INFORMATION: HCDR1
<220> FEATURE:
<221> NAME/KEY: misc_feature
<222> LOCATION: (205)..(234)
<223> OTHER INFORMATION: HCDR2
<220> FEATURE:
<221> NAME/KEY: misc_feature
<222> LOCATION: (346)..(381)
<223> OTHER INFORMATION: HCDR3

<400> SEQUENCE: 14
atgggatgga gctggatctt tctcttcctc ctgtcaggaa ctgcaggtgt ccactctgag      60
gtccagctgc aacagtctgg acctgagctg gtgaagcctg gagcttcaat gaagatatcc     120
tgcaaggctt ctggttactc attcactggc tacaccataa actgggtgaa gcagagccat     180
ggaaagaacc ttgagtggat tggactttt aatccttaca atggtggtac taccttcaac     240
cagaagttca gggcaaggc cacattaact gttgacaagt catccagcac agcctacatg     300
gagctcctca gtctgacatc tgaggactct gcagtctatt actgtgcaag acgatactac     360
ggctacgatg ctatggacta ctggggtcaa ggaacctcag tcaccgtctc ctca           414

<210> SEQ ID NO 15
<211> LENGTH: 138
<212> TYPE: PRT
<213> ORGANISM: Artificial Sequence
<220> FEATURE:
<223> OTHER INFORMATION: 50B5 heavy chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (45)..(54)
```

```
<223> OTHER INFORMATION: HCDR1
<220> FEATURE:
<221> NAME/KEY: MISC_FEATURE
<222> LOCATION: (69)..(78)
<223> OTHER INFORMATION: HCDR2
<220> FEATURE:
<221> NAME/KEY: MISC_FEATURE
<222> LOCATION: (116)..(127)
<223> OTHER INFORMATION: HCDR3

<400> SEQUENCE: 15

Met Gly Trp Ser Trp Ile Phe Leu Phe Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Tyr Thr Ile Asn Trp Val Lys Gln Ser His Gly Lys Asn Leu
    50                  55                  60

Glu Trp Ile Gly Leu Phe Asn Pro Tyr Asn Gly Thr Thr Phe Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Arg Tyr Tyr Gly Tyr Asp Ala Met Asp Tyr Trp
        115                 120                 125

Gly Gln Gly Thr Ser Val Thr Val Ser Ser
    130                 135

<210> SEQ ID NO 16
<211> LENGTH: 396
<212> TYPE: DNA
<213> ORGANISM: Artificial Sequence
<220> FEATURE:
<223> OTHER INFORMATION: 50B5 light chain
<220> FEATURE:
<221> NAME/KEY: misc_feature
<222> LOCATION: (1)..(60)
<223> OTHER INFORMATION: Leader sequence
<220> FEATURE:
<221> NAME/KEY: misc_feature
<222> LOCATION: (130)..(180)
<223> OTHER INFORMATION: LCDR1
<220> FEATURE:
<221> NAME/KEY: misc_feature
<222> LOCATION: (226)..(246)
<223> OTHER INFORMATION: LCDR2
<220> FEATURE:
<221> NAME/KEY: misc_feature
<222> LOCATION: (343)..(366)
<223> OTHER INFORMATION: LCDR3

<400> SEQUENCE: 16
atggaatcac agactcaggt cttcctctcc ctgctgctct gggtatctgg tacctgtggg      60
aacattatga tgacacagtc gccatcatct ctggctgtgt ctgcaggaga aaaggtcact    120
atgagctgta agtccagtca aagtgtttta tacagttcaa atcagaagaa ccacttggcc    180
tggtaccagc agaaaccagg gcagtctcct aaactgctaa tctactgggc atccactagg    240
gaatctggtg tccctgatcg cttcacaggc agtggatctg ggacagattt tactcttacc    300
atcagcagtg tacaagctga agacctggca gtttattact gtcatcaata cctctcctcg    360
tacacgttcg gaggggggac caagctggaa attaag                              396
```

```
<210> SEQ ID NO 17
<211> LENGTH: 132
<212> TYPE: PRT
<213> ORGANISM: Artificial Sequence
<220> FEATURE:
<223> OTHER INFORMATION: 50B5 light chain
<220> FEATURE:
<221> NAME/KEY: MISC_FEATURE
<222> LOCATION: (1)..(20)
<223> OTHER INFORMATION: Leader sequence
<220> FEATURE:
<221> NAME/KEY: MISC_FEATURE
<222> LOCATION: (44)..(60)
<223> OTHER INFORMATION: LCDR1
<220> FEATURE:
<221> NAME/KEY: MISC_FEATURE
<222> LOCATION: (76)..(82)
<223> OTHER INFORMATION: LCDR2
<220> FEATURE:
<221> NAME/KEY: MISC_FEATURE
<222> LOCATION: (115)..(122)
<223> OTHER INFORMATION: LCDR3

<400> SEQUENCE: 17

Met Glu Ser Gln Thr Gln Val Phe Leu Ser Leu Leu Trp Val Ser
1               5                   10                  15

Gly Thr Cys Gly Asn Ile Met Met Thr Gln Ser Pro Ser Ser Leu Ala
            20                  25                  30

Val Ser Ala Gly Glu Lys Val Thr Met Ser Cys Lys Ser Ser Gln Ser
        35                  40                  45

Val Leu Tyr Ser Ser Asn Gln Lys Asn His Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys His Gln Tyr Leu Ser Ser Tyr Thr Phe Gly Gly Gly Thr Lys
        115                 120                 125

Leu Glu Ile Lys
    130

<210> SEQ ID NO 18
<211> LENGTH: 414
<212> TYPE: DNA
<213> ORGANISM: Artificial Sequence
<220> FEATURE:
<223> OTHER INFORMATION: 15B4 heavy chain
<220> FEATURE:
<221> NAME/KEY: misc_feature
<222> LOCATION: (1)..(57)
<223> OTHER INFORMATION: Leader sequence
<220> FEATURE:
<221> NAME/KEY: misc_feature
<222> LOCATION: (133)..(162)
<223> OTHER INFORMATION: HCDR1
<220> FEATURE:
<221> NAME/KEY: misc_feature
<222> LOCATION: (208)..(237)
<223> OTHER INFORMATION: HCDR2
<220> FEATURE:
<221> NAME/KEY: misc_feature
<222> LOCATION: (346)..(381)
<223> OTHER INFORMATION: HCDR3

<400> SEQUENCE: 18
```

```
atggaatgga gctgggtctt tctcttcctg atggcagtgg ttacaggggt caattcagag    60
gttcagctgc agcagtctgg ggctgaggtt gtgaggccag gggccttagt caagttgtcc   120
tgcaaagctt ctggcttcaa cattaaagac tactatatgc actgggtgag gcagaggcct   180
gaacagggcc tggagtggat tgatggatt gatcctgaga atgacaatac tatatatgac   240
ccgaagttcc aggacagggc cagtataaca gcagacacat cctccaacac agcctacctg   300
cagctcagca gcctgacatc tgaggacact gccgtctatt actgtgctag ggacttcggc   360
tacgtagcct ggcttgttta ctggggccaa gggactctgg tcactgtctc tgca          414
```

<210> SEQ ID NO 19
<211> LENGTH: 138
<212> TYPE: PRT
<213> ORGANISM: Artificial Sequence
<220> FEATURE:
<223> OTHER INFORMATION: 15B4 heavy chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (45)..(54)
<223> OTHER INFORMATION: HCDR1
<220> FEATURE:
<221> NAME/KEY: MISC_FEATURE
<222> LOCATION: (69)..(79)
<223> OTHER INFORMATION: HCDR2
<220> FEATURE:
<221> NAME/KEY: MISC_FEATURE
<222> LOCATION: (116)..(127)
<223> OTHER INFORMATION: HCDR3

<400> SEQUENCE: 19

Met Glu Trp Ser Trp Val Phe Leu Phe Leu Met Ala Val Val Thr Gly
1               5                   10                  15

Val Asn Ser Glu Val Gln Leu Gln Gln Ser Gly Ala Glu Val Val Arg
            20                  25                  30

Pro Gly Ala Leu Val Lys Leu Ser Cys Lys Ala Ser Gly Phe Asn Ile
        35                  40                  45

Lys Asp Tyr Tyr Met His Trp Val Arg Gln Arg Pro Glu Gln Gly Leu
    50                  55                  60

Glu Trp Ile Gly Trp Ile Asp Pro Glu Asn Asp Asn Thr Ile Tyr Asp
65                  70                  75                  80

Pro Lys Phe Gln Asp Arg Ala Ser Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Arg Asp Phe Gly Tyr Val Ala Trp Leu Val Tyr Trp
        115                 120                 125

Gly Gln Gly Thr Leu Val Thr Val Ser Ala
    130                 135

<210> SEQ ID NO 20
<211> LENGTH: 378
<212> TYPE: DNA
<213> ORGANISM: Artificial Sequence
<220> FEATURE:
<223> OTHER INFORMATION: 15B4 light chain
<220> FEATURE:
<221> NAME/KEY: misc_feature
<222> LOCATION: (1)..(57)
<223> OTHER INFORMATION: Leader sequence
<220> FEATURE:

```
<221> NAME/KEY: misc_feature
<222> LOCATION: (127)..(159)
<223> OTHER INFORMATION: LCDR1
<220> FEATURE:
<221> NAME/KEY: misc_feature
<222> LOCATION: (205)..(225)
<223> OTHER INFORMATION: LCDR2
<220> FEATURE:
<221> NAME/KEY: misc_feature
<222> LOCATION: (322)..(345)
<223> OTHER INFORMATION: LCDR3

<400> SEQUENCE: 20
atgtcacagt ctcaggtctt tgtattcgcg tttctctggt tgtctggtgt tgatggagac      60
attgtgatga cccagtctca agaattcatg tccacatcag taggagacag ggtcagcatc     120
acctgcaagg ccagtcagaa tgtggatact gctgtagcct ggtatcaaca gaaaccagga     180
caatctccta aactactgat ttactcggca tccaatcggt acactggagt ccctgatcgc     240
ttcacaggca ctggatctgg gacagatttc actctcacca tcaacaatat gcagtctgaa     300
gacctggcag attatttctg ccagcaatat agcagctatc cacgttcgg agggaggacc      360 aagctggaaa taaaacgg                                                   378

<210> SEQ ID NO 21
<211> LENGTH: 126
<212> TYPE: PRT
<213> ORGANISM: Artificial Sequence
<220> FEATURE:
<223> OTHER INFORMATION: 15B4 light chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (43)..(53)
<223> OTHER INFORMATION: LCDR1
<220> FEATURE:
<221> NAME/KEY: MISC_FEATURE
<222> LOCATION: (69)..(75)
<223> OTHER INFORMATION: LCDR2
<220> FEATURE:
<221> NAME/KEY: MISC_FEATURE
<222> LOCATION: (107)..(115)
<223> OTHER INFORMATION: LCDR3

<400> SEQUENCE: 21

Met Ser Gln Ser Gln Val Phe Val Phe Ala Phe Leu Trp Leu Ser Gly
 1               5                  10                  15

Val Asp Gly Asp Ile Val Met Thr Gln Ser Gln Glu Phe Met Ser Thr
             20                  25                  30

Ser Val Gly Asp Arg Val Ser Ile Thr Cys Lys Ala Ser Gln Asn Val
         35                  40                  45

Asp Thr Ala Val Ala Trp Tyr Gln Gln Lys Pro Gly Gln Ser Pro Lys
     50                  55                  60

Leu Leu Ile Tyr Ser Ala Ser Asn Arg Tyr Thr Gly Val Pro Asp Arg
 65                  70                  75                  80

Phe Thr Gly Thr Gly Ser Gly Thr Asp Phe Thr Leu Thr Ile Asn Asn
                 85                  90                  95

Met Gln Ser Glu Asp Leu Ala Asp Tyr Phe Cys Gln Gln Tyr Ser Ser
            100                 105                 110

Tyr Pro Thr Phe Gly Gly Arg Thr Lys Leu Glu Ile Lys Arg
        115                 120                 125
```

```
<210> SEQ ID NO 22
<211> LENGTH: 111
<212> TYPE: PRT
<213> ORGANISM: Artificial Sequence
<220> FEATURE:
<223> OTHER INFORMATION: IgV domain

<400> SEQUENCE: 22

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
    50                  55                  60

Gly Asp Phe Arg Lys Gly Asp Val Ser Leu Thr Ile Glu Asn Val Thr
65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala
            100                 105                 110
```